(12) United States Patent
Song et al.

(10) Patent No.: US 11,422,123 B2
(45) Date of Patent: Aug. 23, 2022

(54) FIELD CONDITION-BASED EXPERIMENTAL APPARATUS AND METHOD FOR ECOLOGICAL INDICATOR OF VEGETATION

(71) Applicants: China Institute of Water Resources and Hydropower Research, Beijing (CN); Beijing Water Science and Technology Institute, Beijing (CN); Yellow River Conservancy Commission of the Ministry of Water Resources, Zhengzhou (CN)

(72) Inventors: Yifan Song, Beijing (CN); Yajing Lu, Beijing (CN); Yu Wang, Zhengzhou (CN); Denghua Yan, Beijing (CN); Tiejun Liu, Beijing (CN); Jianying Guo, Beijing (CN); Tianling Qin, Beijing (CN); Baisha Weng, Beijing (CN)

(73) Assignees: China Institute of Water Resources and Hydropower Research, Beijing (CN); Beijing Water Science and Technology Institute, Beijing (CN); YELLOW RIVER CONSERVANCY COMMISSION OF THE MINISTRY OF WATER RESOURCES, Zhengzhou (CN)

( * ) Notice: Subject to any disclaimer, the term of this patent is extended or adjusted under 35 U.S.C. 154(b) by 0 days.

(21) Appl. No.: 17/456,167

(22) Filed: Nov. 23, 2021

(65) Prior Publication Data
US 2022/0170902 A1 Jun. 2, 2022

(30) Foreign Application Priority Data
Nov. 27, 2020 (CN) .......................... 202011358117.9

(51) Int. Cl.
*G01N 33/24* (2006.01)
*A01B 79/02* (2006.01)
*A01B 79/00* (2006.01)

(52) U.S. Cl.
CPC .......... *G01N 33/246* (2013.01); *A01B 79/005* (2013.01); *A01B 79/02* (2013.01)

(58) Field of Classification Search
CPC ...... G01N 33/246; G01N 33/24; G01N 33/00; A01B 79/005; A01B 79/02; A01B 79/00
See application file for complete search history.

(56) References Cited

FOREIGN PATENT DOCUMENTS

CN 203629923 U 6/2014
CN 204851241 U 12/2015
(Continued)

*Primary Examiner* — Christopher J. Novosad
(74) *Attorney, Agent, or Firm* — Bayramoglu Law Offices LLC

(57) ABSTRACT

A field condition-based experimental apparatus for an ecological indicator of vegetation includes a plurality of isolation units arranged at intervals and an auxiliary mechanism detachably connected to the isolation unit. The isolation units include a plurality of isolation boxes arranged at intervals and respectively having a hollow structure, and a support frame respectively disposed at four corners of the isolation box. The auxiliary mechanism is detachably connected to the support frame. A soil layer is disposed in the isolation box. The experimental apparatus has a reliable structure and is easy to use. An appropriate number of isolation units are buried under field conditions based on experimental needs. Auxiliary mechanisms of different structures are mounted based on experimental conditions. This implements reliable detection of an ecological indicator of vegetation under the field conditions and effectively improves authenticity and reliability of detection results. The auxiliary mechanism facilitates disassembly and assembly.

7 Claims, 3 Drawing Sheets

(56) References Cited

FOREIGN PATENT DOCUMENTS

| CN | 105961176 | A | 9/2016 |
| CN | 106769262 | A | 5/2017 |
| CN | 206638464 | U | 11/2017 |
| CN | 206945006 | U | 1/2018 |
| CN | 207114511 | U | 3/2018 |
| CN | 107957279 | A | 4/2018 |
| CN | 207742184 | U | 8/2018 |
| CN | 209745580 | U | 12/2019 |
| CN | 110780039 | A | 2/2020 |

FIELD CONDITION-BASED EXPERIMENTAL APPARATUS AND METHOD FOR ECOLOGICAL INDICATOR OF VEGETATION

CROSS REFERENCE TO THE RELATED APPLICATIONS

This application is based upon and claims priority to Chinese Patent Application No. 202011358117.9, filed on Nov. 27, 2020, the entire contents of which are incorporated herein by reference.

TECHNICAL FIELD

The present invention relates to the technical field of ecological environment, and more particularly, to a field condition-based experimental apparatus and method for an ecological indicator of vegetation.

BACKGROUND

The developing trends of experimental research on vegetation physiology, ecology, and hydrology is to focus more on controlled or semi-controlled experiments under field conditions in order to obtain the mechanisms and laws closest to that in nature. Natural states that have been carried out in the past, however, are usually ignored or destroyed in manually controlled indoor experiments. This greatly affects the reliability, authenticity, and accuracy of ecological research of vegetation under field conditions.

SUMMARY

The present invention provides a field condition-based experimental apparatus and method for an ecological indicator of vegetation to resolve a problem that existing field condition-based experiments for an ecological indicator of vegetation have low authenticity and reliability.

To resolve the foregoing technical problem, the present invention adopts the following technical solution: a field condition-based experimental apparatus for an ecological indicator of vegetation is provided. The apparatus includes a plurality of isolation units arranged at intervals and an auxiliary mechanism detachably connected to the isolation unit.

The isolation units include a plurality of isolation boxes arranged at intervals and respectively having a hollow structure, and a support frame respectively disposed at four corners of the isolation box. The auxiliary mechanism is detachably connected to the support frame. A soil layer is disposed in the isolation box.

The beneficial effects of the foregoing technical solution are as follows: The experimental apparatus has a reliable structure and is easy to use. An appropriate number of isolation units are buried under field conditions based on experimental needs. Auxiliary mechanisms of different structures are mounted based on experimental conditions. This implements reliable detection of an ecological indicator of vegetation under the field conditions and effectively improves authenticity and reliability of detection results. In addition, the auxiliary mechanism is detachably connected to the isolation box to facilitate disassembly and assembly, and improve work efficiency.

Further, the isolation box may include a pre-buried portion and a fencing portion integrally connected to the pre-buried portion. The pre-buried portion is buried in soil. The fencing portion extends out of the soil. The support frame is respectively disposed at four corners of the fencing portion.

The beneficial effects of the foregoing technical solution are as follows: A structure of the isolation box is set to form the pre-buried portion and the fencing portion. The pre-buried portion is buried in the soil to provide a reliable and stable foundation. The fencing portion forms a growth isolation area for vegetation in natural states. Experiments are carried out inside the fencing portion with good performance.

Further, the support frame may include a support tube respectively disposed at the four corners of the fencing portion and a support rod nested in the support tube in a fitting manner. A limiting ring is connected to an outer wall of the support rod in the fitting manner.

The beneficial effects of the foregoing technical solution are as follows: The support frame provides a reliable support foundation for the auxiliary mechanism. A structure of the support frame is set such that when the apparatus is being used, the support rod is inserted into the support tube to support the auxiliary mechanism. The limiting ring is adjusted up and down to adjust a depth of the support rod inserted into the support tube. This is convenient and reliable.

Further, the outer wall of the support rod may be provided with an outer thread, and an inner wall of the limiting ring may be provided with an inner thread matched with the outer thread. The limiting ring is connected to the support rod through the threads.

The beneficial effects of the foregoing technical solution are as follows: The support rod is in threaded connection to the limiting ring. The threaded connection has a self-locking function and is reliable in locking. The limiting ring is used to adjust the depth of the support rod inserted into the support tube. Such adjustment is reliable and stable.

Further, the support rod may include a nested portion and a threaded portion integrally connected to the nested portion. The nested portion is nested in the support tube in the fitting manner. The threaded portion extends out of the support tube. The limiting ring is connected to the threaded portion in the fitting manner.

The beneficial effects of the foregoing technical solution are as follows: A structure of the support rod is set to form the nested portion and the threaded portion. An outer wall of the nested portion is not provided with a thread to achieve reliable fitting between the support rod and the support tube. The threaded portion and the limiting ring cooperate to adjust a height.

Further, a transparent tube may be obliquely inserted into the soil layer, an end of the transparent tube may extend out of the isolation box, and a plurality of soil moisture meters may be sequentially disposed from top to bottom in the soil layer.

The beneficial effects of the foregoing technical solution are as follows: A growth status of vegetation roots in the isolation unit can be intuitively monitored through the transparent tube. The soil moisture meters are used to detect soil moisture in the isolation unit, and are disposed from top to bottom to detect moisture in different layers of soil in the isolation unit.

Further, the auxiliary mechanism may include a transparent waterproof plate, and four corners of the transparent waterproof plate are respectively connected to the support rod in the fitting manner.

The beneficial effects of the foregoing technical solution are as follows: The auxiliary mechanism forms an experimental condition such as drought, no rain, or no snow. Control groups and experimental groups are set to carry out repeated experiments for comparison, so as to obtain impact of different conditions on ecological growth of vegetation. In addition, a gap is formed between the transparent waterproof plate and the isolation unit to ensure natural circulation of air. The waterproof plate is made of transparent material to ensure penetration of sunlight and improve reliability and accuracy of the experiments.

Further, the auxiliary mechanism may include a water tank and a first sleeve tube respectively disposed at four corners of the water tank. A bottom plate of the water tank is provided with through holes distributed uniformly.

The beneficial effects of the foregoing technical solution are as follows: The auxiliary mechanism forms artificial experimental conditions, such as artificial rainfall, water and fertilizer, or different concentrations of solutes. The water tank is filled with different volumes of water based on experimental requirements to simulate different levels of precipitation. The water passes through the through holes in the bottom plate and drips from top to bottom to form uniformly distributed artificial precipitation. Differences in (physical, chemical, and biological) soil properties and vegetation physiological and ecological indicators in isolation plots on which different precipitation treatments are performed are tested to further identify whether different levels of precipitation have impact on the growth and development of the vegetation and the soil properties.

The present invention further provides an experimental method for a field condition-based experimental apparatus for an ecological indicator of vegetation, including the following steps:

step 1: setting a plurality of gradient treatment groups and control groups based on experimental conditions;

step 2: performing simulation tests on the treatment groups under different conditions, and determining test results; and step 3: comparing the test results of the treatment groups with the control groups to obtain influence factors to growth of the vegetation under the different conditions.

The beneficial effects of the foregoing technical solution are as follows: The method is reliable in operation, good in performance, and accurate and reliable in measurement. Impact on growth of the vegetation and soil properties under different experimental conditions are formed by setting the plurality of control groups and treatment groups.

Further, the step of setting the treatment groups in step 1 may include the following steps:

step 1.1: excavating a trench in soil, burying the pre-buried portion of the isolation box in the trench, and backfilling the soil to allow the fencing portion to extend out of the soil;

step 1.2: inserting the transparent tube and the soil moisture meters into the soil layer in the isolation box, and communicatively connecting the soil moisture meters to a measurement instrument; and step 1.3: mounting the auxiliary mechanism on the support rod, and simulating impact of different field conditions on growth of the vegetation by using the auxiliary mechanism.

The present invention has the following beneficial effects: The present invention provides the experimental apparatus and method for a vegetation biological indicator under field conditions. The experimental apparatus has a reliable structure and is easy to use. The appropriate number of isolation units are buried under the field conditions based on the experimental needs. The auxiliary mechanisms of different structures are mounted based on the experimental conditions. This implements the reliable detection of the vegetation ecological indicator under the field conditions and effectively improves the authenticity and reliability of the detection results. The method is reliable in operation, good in performance, and accurate and reliable in measurement. Impact on growth of the vegetation and soil properties under different experimental conditions are formed by setting the plurality of control groups and treatment groups. In addition, the auxiliary mechanism is detachably connected to the isolation box to facilitate disassembly and assembly, and improve work efficiency.

Figure 1:
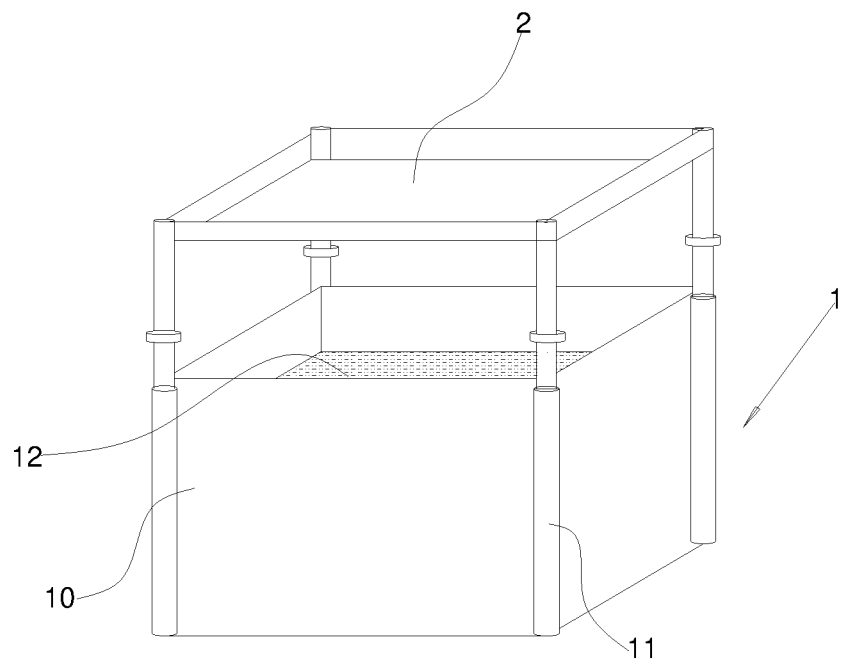
FIG. 1 is a schematic structural diagram of the present invention.

Reference numerals in FIG. 1 to FIG. 5: 1—isolation unit, 2—auxiliary mechanism, 10—isolation box, 11—support frame, 12—soil layer, 101—pre-buried portion, 102—fencing portion, 111—support rod, 112—limiting ring, 113—nested portion, 114—threaded portion, 13—transparent tube, 14—soil moisture meter, 20—transparent waterproof plate, 21—water tank, and 22—first sleeve tube.

DETAILED DESCRIPTION OF THE EMBODIMENTS

The principles and features of the present invention are described below with reference to the accompanying drawings. The listed embodiments serve only to explain the present invention, rather than to limit the scope of the present invention.

Figure 2:
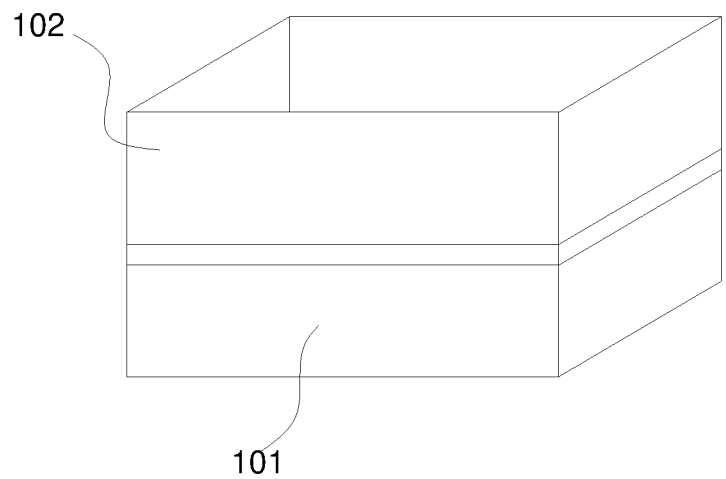
FIG. 2 is a schematic structural diagram of an isolation unit according to the present invention.

As shown in FIG. 1 and FIG. 2, a field condition-based experimental apparatus for an ecological indicator of vegetation includes a plurality of isolation units 1 arranged at intervals and an auxiliary mechanism 2 detachably connected to the isolation unit 1.

The isolation units 1 include a plurality of isolation boxes 10 arranged at intervals and respectively having a hollow structure, and a support frame 11 respectively disposed at four corners of the isolation box 10. The auxiliary mechanism 2 is detachably connected to the support frame 11. A soil layer 12 is disposed in the isolation box 10.

The experimental apparatus has a reliable structure and is easy to use. An appropriate number of isolation units 1 are buried under field conditions based on experimental needs. Auxiliary mechanisms 2 of different structures are mounted based on experimental conditions. This implements reliable detection of an ecological indicator of vegetation under the field conditions and effectively improves authenticity and reliability of detection results. In addition, the auxiliary mechanism 2 is detachably connected to the isolation box 10 to facilitate disassembly and assembly, and improve work efficiency.

The isolation box 10 includes a pre-buried portion 101 and a fencing portion 102 integrally connected to the pre-buried portion 101. The pre-buried portion (101) is buried in soil. The fencing portion 102 extends out of the soil. The support frame 11 is respectively disposed at four corners of the fencing portion 102. A structure of the isolation box 10 is set to form the pre-buried portion 101 and the fencing portion 102. The pre-buried portion 101 is buried in the soil to provide a reliable and stable foundation. The fencing portion 102 forms a growth isolation area for vegetation in natural states. Experiments are carried out inside the fencing portion 102 with good performance.

The support frame 11 includes a support tube 110 respectively disposed at the four corners of the fencing portion 102 and a support rod 111 nested in the support tube 110 in a fitting manner. A limiting ring 112 is connected to an outer wall of the support rod 111 in the fitting manner. The support frame 11 provides a reliable support foundation for the auxiliary mechanism 2. A structure of the support frame 11 is set such that when the apparatus is being used, the support rod 111 is inserted into the support tube 110 to support the auxiliary mechanism 2. The limiting ring 112 is adjusted up and down to adjust a depth of the support rod 111 inserted into the support tube 110. This is convenient and reliable.

The outer wall of the support rod 111 is provided with an outer thread. An inner wall of the limiting ring 112 is provided with an inner thread matched with the outer thread. The limiting ring 112 is connected to the support rod 111 through the threads. The support rod 111 is in threaded connection to the limiting ring 112. The threaded connection has a self-locking function and is reliable in locking. The limiting ring 112 is used to adjust the depth of the support rod 111 inserted into the support tube 110. Such adjustment is reliable and stable.

The support rod 111 may include a nested portion 113 and a threaded portion 114 integrally connected to the nested portion 113. The nested portion 113 is nested in the support tube 110 in the fitting manner. The threaded portion 114 extends out of the support tube 110. The limiting ring 112 is connected to the threaded portion 114 in the fitting manner. A structure of the support rod 111 is set to form the nested portion 113 and the threaded portion 114. An outer wall of the nested portion 113 is not provided with a thread to achieve reliable fitting between the support rod 111 and the support tube 110. The threaded portion 114 and the limiting ring 112 cooperate to adjust a height.

Figure 3:
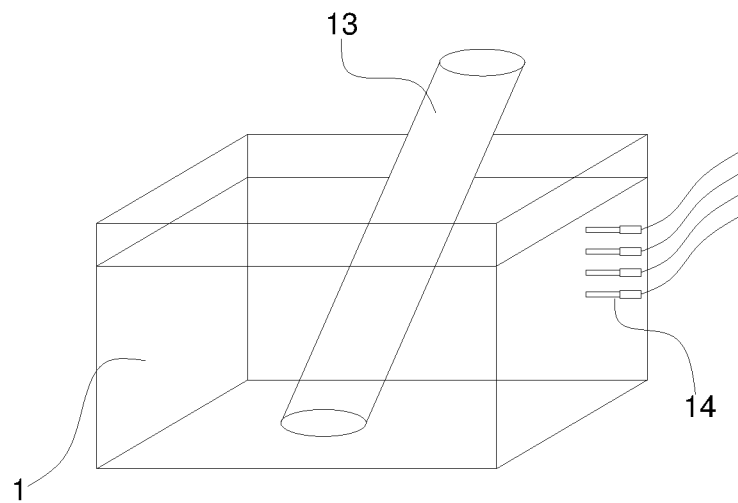
FIG. 3 is a schematic diagram of Embodiment 1 according to the present invention.

Embodiment 1: As shown in FIG. 3, a transparent tube 13 is obliquely inserted into the soil layer 12, an end of the transparent tube 13 extends out of the isolation box 10, and a plurality of soil moisture meters 14 are sequentially disposed from top to bottom in the soil layer 12. A growth status of vegetation roots in the isolation unit 1 can be intuitively monitored through the transparent tube 13. The soil moisture meters 14 are used to detect soil moisture in the isolation unit 1, and are disposed from top to bottom to detect moisture in different layers of soil in the isolation unit 1.

Figure 4:
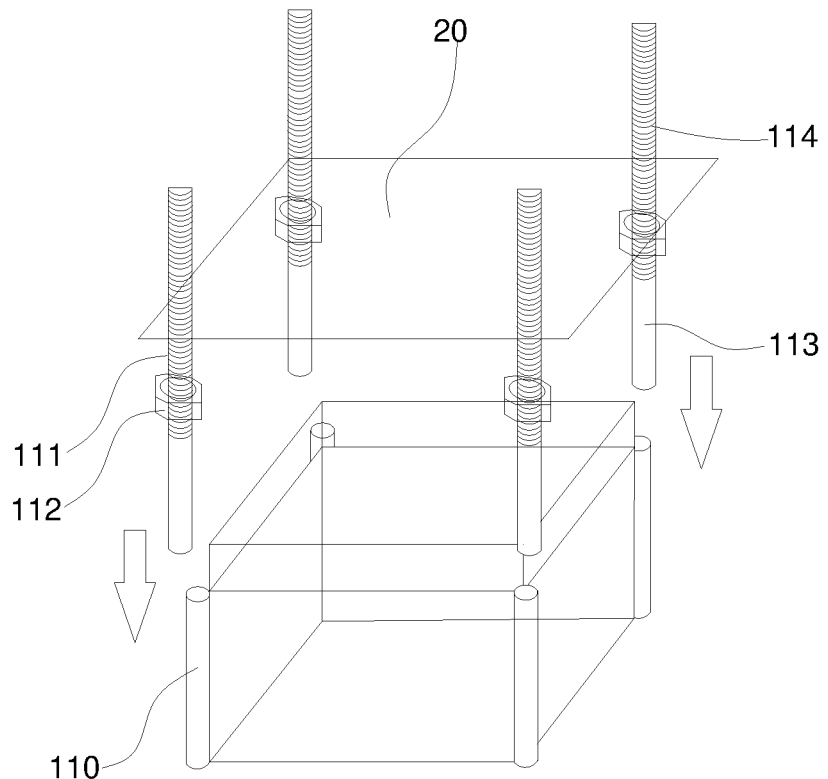
FIG. 4 is a schematic diagram of Embodiment 2 according to the present invention.

Embodiment 2: As shown in FIG. 4, the auxiliary mechanism 2 includes a transparent waterproof plate 20, and four corners of the transparent waterproof plate 20 are respectively connected to the support rod 111 in the fitting manner. The auxiliary mechanism 2 forms an experimental condition such as drought, no rain, or no snow. Control groups and experimental groups are set to carry out repeated experiments for comparison, so as to obtain impact of different conditions on ecological growth of vegetation. In addition, a gap is formed between the transparent waterproof plate 20 and the isolation unit 1 to ensure natural circulation of air. The waterproof plate is made of transparent material to ensure penetration of sunlight and improve reliability and accuracy of the experiments.

Figure 5:
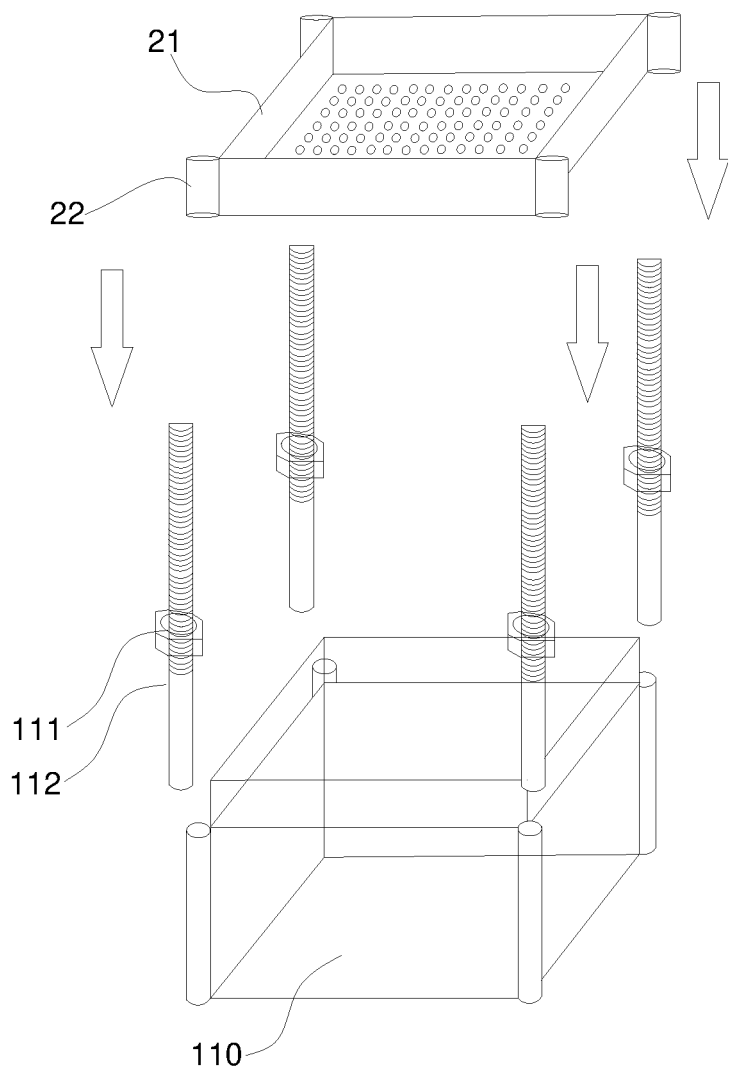
FIG. 5 is a schematic diagram of Embodiment 3 according to the present invention.

Embodiment 3: As shown in FIG. 5, the auxiliary mechanism 2 includes a water tank 21 and a first sleeve tube 22 respectively disposed at four corners of the water tank 21. A bottom plate of the water tank 21 is provided with through holes distributed uniformly. The auxiliary mechanism 2 forms artificial experimental conditions, such as artificial rainfall, water and fertilizer, or different concentrations of solutes. The water tank 21 is filled with different volumes of water based on experimental requirements to simulate different levels of precipitation. The water passes through the through holes in the bottom plate and drips from top to bottom to form uniformly distributed artificial precipitation. Differences in physical, chemical, and biological soil properties, and vegetation physiological and ecological indicators in isolation plots on which different precipitation treatments are performed are tested to further identify whether different levels of precipitation have impact on the growth and development of the vegetation and the soil properties.

The present invention further provides an experimental method for a field condition-based experimental apparatus for an ecological indicator of vegetation, including the following steps:

Step 1: Set a plurality of gradient treatment groups and control groups based on experimental conditions.

Step 2: Perform simulation tests on the treatment groups under different conditions, and determine test results.

Step 3: Compare the test results of the treatment groups with the control groups to obtain influence factors to growth of the vegetation under the different conditions.

The method is reliable in operation, good in performance, and accurate and reliable in measurement. Impact on growth of the vegetation and soil properties under different experimental conditions are formed by setting the plurality of control groups and treatment groups.

Further, the step of setting the treatment groups in step 1 may include the following steps:

Step 1.1: Excavate a trench in soil, bury the pre-buried portion 101 of the isolation box 10 in the trench, and backfill the soil to allow the fencing portion 102 to extend out of the soil.

Step 1.2: Insert the transparent tube 13 and the soil moisture meters 14 into the soil layer 12 in the isolation box 10, and communicatively connect the soil moisture meters 14 to a measurement instrument.

Step 1.3: Mount the auxiliary mechanism 2 on the support rod 111, and simulate impact of different field conditions on growth of the vegetation by using the auxiliary mechanism 2.

The foregoing descriptions are merely preferred embodiments of the present invention, and are not intended to limit the present invention. Any modifications, equivalent replacements, improvements, and the like made within the spirit and principle of the present invention shall be all included in the protection scope of the present invention.

What is claimed is:

1. A field condition-based experimental apparatus for an ecological indicator of vegetation, comprising a plurality of isolation units arranged at intervals and an auxiliary mechanism detachably connected to the isolation unit; wherein
the isolation units comprise a plurality of isolation boxes arranged at intervals and respectively having a hollow structure, and a support frame respectively disposed at four corners of the isolation box; the auxiliary mechanism is detachably connected to the support frame; and a soil layer is disposed in the isolation box;
the isolation box comprises a pre-buried portion and a fencing portion integrally connected to the pre-buried portion, the pre-buried portion is buried in soil, the fencing portion extends out of the soil, and the support frame is respectively disposed at four corners of the fencing portion;

the support frame comprises a support tube respectively disposed at the four corners of the fencing portion and a support rod nested in the support tube in a fitting manner, and a limiting ring is connected to an outer wall of the support rod in the fitting manner;

the outer wall of the support rod is provided with an outer thread, an inner wall of the limiting ring is provided with an inner thread matched with the outer thread, and the limiting ring is connected to the support rod through the threads; and the auxiliary mechanism comprises a transparent waterproof plate, four corners of the transparent waterproof plate are respectively connected to the support rod in the fitting manner, and a gap is formed between the transparent waterproof plate and the isolation unit to ensure natural circulation of air.

2. The field condition-based experimental apparatus for the ecological indicator of the vegetation according to claim 1, wherein the support rod comprises a nested portion and a threaded portion integrally connected to the nested portion, the nested portion is nested in the support tube in the fitting manner, the threaded portion extends out of the support tube, and the limiting ring is connected to the threaded portion in the fitting manner.

3. The field condition-based experimental apparatus for the ecological indicator of the vegetation according to claim 1, wherein a transparent tube is obliquely inserted into the soil layer, an end of the transparent tube extends out of the isolation box, and a plurality of soil moisture meters are sequentially disposed from top to bottom in the soil layer.

4. An experimental method based on the field condition-based experimental apparatus for the ecological indicator of the vegetation according to 1, comprising the following steps:

step 1: setting a plurality of gradient treatment groups and control groups based on experimental conditions;

step 2: performing simulation tests on the treatment groups under different conditions, and determining test results; and step 3: comparing the test results of the treatment groups with the control groups to obtain influence factors to growth of the vegetation under the different conditions.

5. The experimental method based on the field condition-based experimental apparatus for the ecological indicator of the vegetation according to claim 4, wherein the step of setting the treatment groups in step 1 comprises the following steps:

step 1.1: excavating a trench in soil, burying a pre-buried portion of the isolation box in the trench, and backfilling the soil to allow a fencing portion to extend out of the soil;

step 1.2: inserting a transparent tube and soil moisture meters into a soil layer in the isolation box, and communicatively connecting the soil moisture meters to a measurement instrument; and step 1.3: mounting the auxiliary mechanism on a support rod, and simulating impact of different field conditions on growth of the vegetation by using the auxiliary mechanism.

6. The experimental method according to claim 4, wherein the support rod comprises a nested portion and a threaded portion integrally connected to the nested portion, the nested portion is nested in the support tube in the fitting manner, the threaded portion extends out of the support tube, and the limiting ring is connected to the threaded portion in the fitting manner.

7. The experimental method according to claim 4, wherein a transparent tube is obliquely inserted into the soil layer, an end of the transparent tube extends out of the isolation box, and a plurality of soil moisture meters are sequentially disposed from top to bottom in the soil layer.

* * * * *